US00PP36234P2

(12) United States Plant Patent
Berry

(10) Patent No.: US PP36,234 P2
(45) Date of Patent: Nov. 5, 2024

(54) WAX MYRTLE PLANT NAMED 'JBG 1000'

(50) Latin Name: *Myrica cerifera*
Varietal Denomination: JBG 1000

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/491,326

(22) Filed: Oct. 20, 2023

(51) Int. Cl.
*A01H 6/00* (2018.01)
*A01H 5/12* (2018.01)

(52) U.S. Cl.
USPC ..... Plt./226

(58) Field of Classification Search
USPC ..... Plt./226
CPC ..... A01H 6/00; A01H 5/12
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of Wax Myrtle plant named 'JBG 1000' that is distinguishable by its highly vigorous growth, high resistance to heat and humidity, and foliage has a pleasant fragrance and is a vibrant light green color.

2 Drawing Sheets

Genus and species: *Myrica cerifera.*
Variety denomination: 'JBG 1000'.

BACKGROUND

The present disclosure relates to a new and distinct cultivar of *Myrica cerifera* plant, commonly known as Wax Myrtle, an evergreen shrub that is grown for use as an ornamental landscape and container plant. The new variety is known botanically as *Myrica cerifera* and will be referred to hereinafter by the cultivar name 'JBG 1000'.

'JBG 1000' originated and was selected from a population of seedlings from an unknown female parent and an unknown male parent in 2017 in Houston, Texas.

'JBG 1000' was first asexually propagated under the control of the inventors in 2017 in a greenhouse in Grand Saline, Texas, using softwood cuttings. The inventors have confirmed that 'JBG 1000' is stable and reproduces true to type in successive generations of asexual reproduction.

SUMMARY

The following traits have been repeatedly observed and represent the distinguishing characteristics of 'JBG 1000'. 'JBG 1000' has not been tested under all possible conditions, and phenotypic differences may be observed with variations in environmental, climatic, and cultural conditions, without, however, any variance in genotype.

1. Highly vigorous;
2. Highly tolerant to heat and humidity; and
3. Foliage has a pleasant fragrance to it and is a vibrant light green color.

DESCRIPTION OF THE PHOTOGRAPHS

The accompanying color photographs illustrate the overall appearance of the new *Myrica cerifera* cultivar 'JBG 1000', showing the colors as true as it is reasonably possible to obtain in colored reproductions of this type. Photographs were taken in August 2023 in Carpinteria, California, from a twenty-four-month-old plant grown outdoors in a 2-gallon container. Colors in the photographs may differ from the color values cited in the detailed botanical description, which more accurately describes the actual colors of the new variety 'JBG 1000'.

DESCRIPTION OF THE NEW VARIETY

Figure 1:
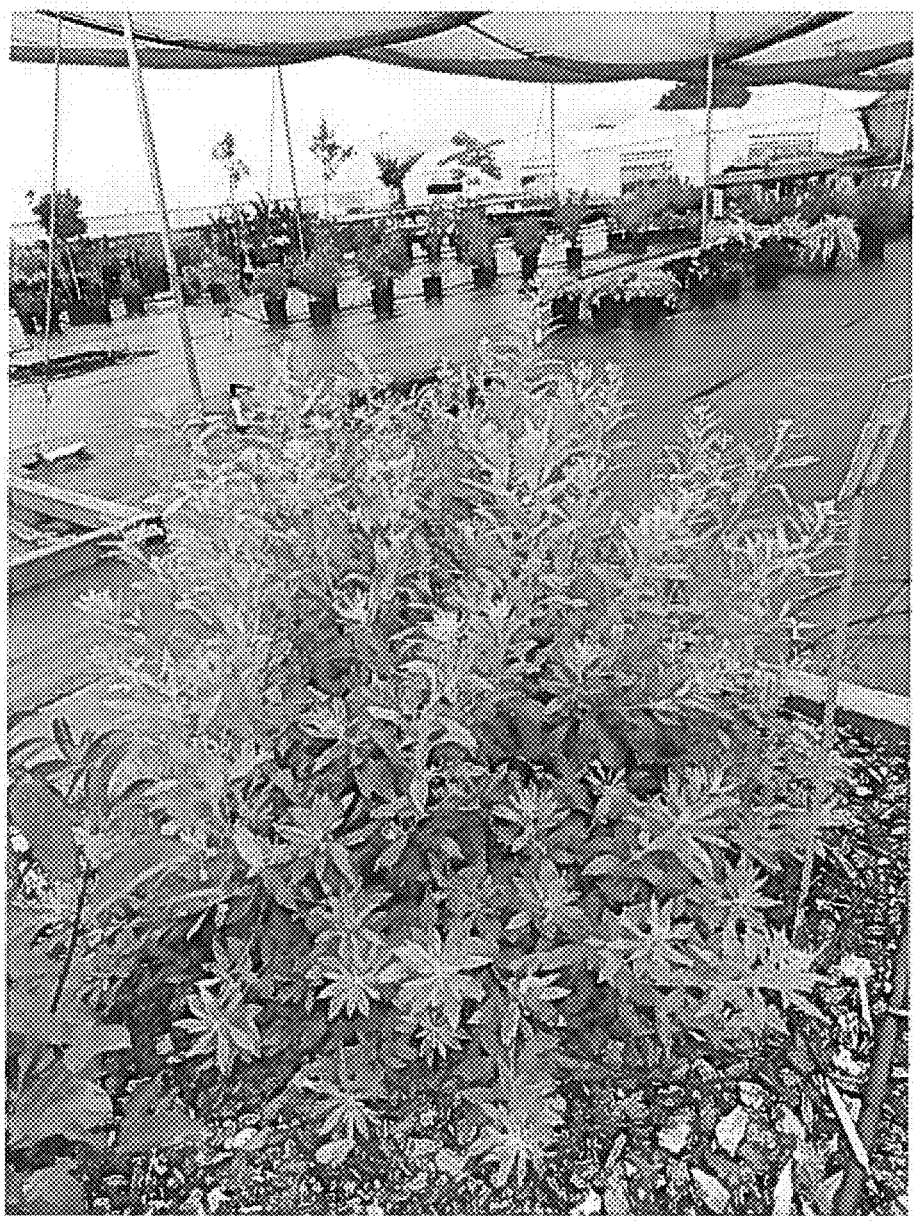
FIG. 1 depicts an entire plant in flower of 'JBG 1000'.
Figure 2:
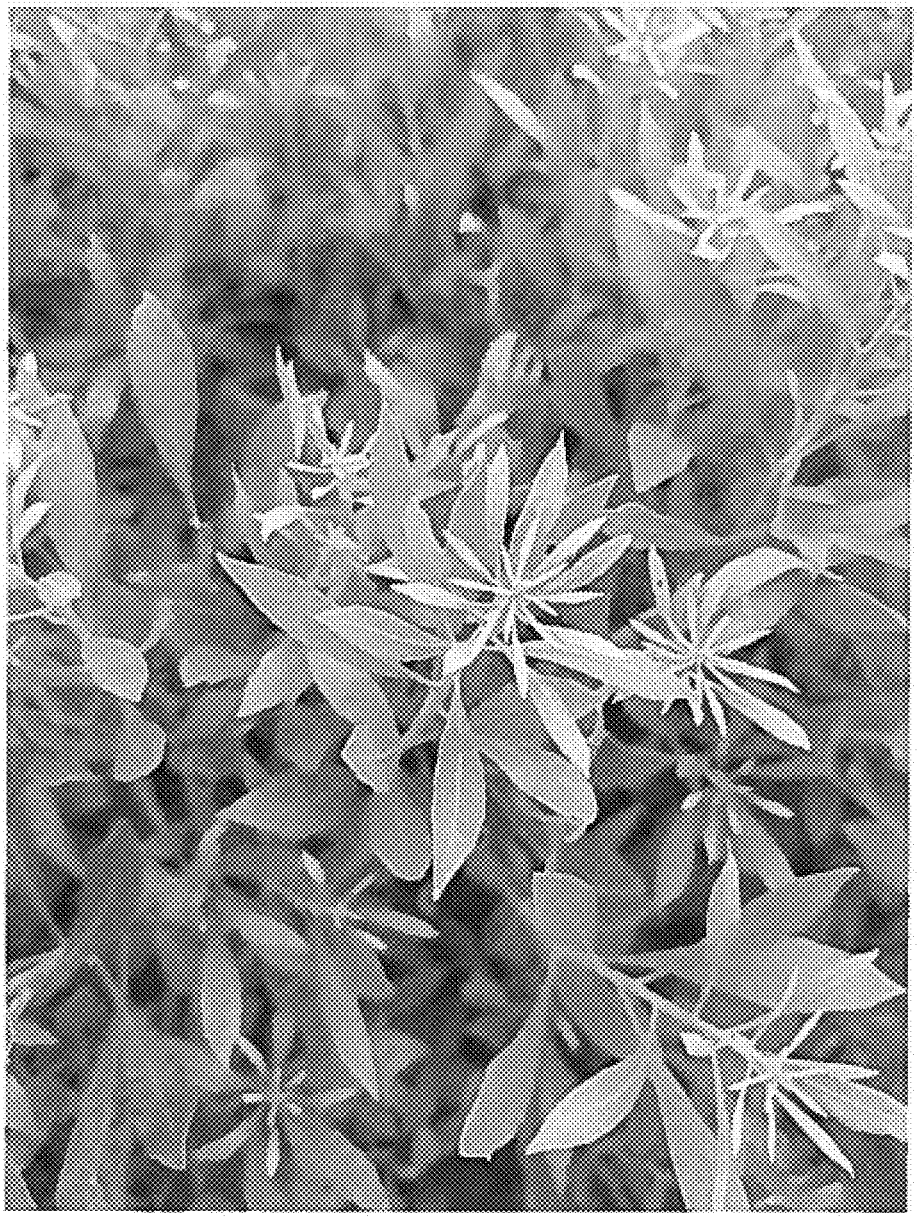
FIG. 2 depicts a close-up view of the young leaves of 'JBG 1000'.

The following detailed descriptions set forth the distinctive characteristics of 'JBG 1000'. Observations, measurements, values, and comparisons were collected in 2023 in Grand Saline, Texas, from a 12-week-old plant which was growing outdoors in full sun in a 2-gallon container. Color determinations were made in accordance with The 2007 Royal Horticultural Society Colour Chart from London, England, except where general color terms of ordinary dictionary significance are used.

Classification:
- *Family.*—Myriaceae.
- *Genus.*—*Myrica.*
- *Species.*—*cerifera.*
- *Common name.*—Wax Myrtle.

Parentage:
- *Female parent.*—Unknown.
- *Male parent.*—Unknown.

Plant:
- *Type shrub.*—Perennial.
- *Vigor.*—High.
- *Habit.*—Moderately upright but free branching habits, dense.
- *Plant dimensions* (*after* 1 *year*).—2.5'×1.5'.
- *Plant dimensions* (*mature*).—13'×10'.
- *Hardiness USDA zone.*—7 to 10.
- *Root system type.*—Fibrous.

*Root color.*—199C.
*Recommended soil and growing conditions.*—Moderately fertile, well-drained soil.
*Recommended light conditions* (*sun, shade*).—Full sun.
*Crop time.*—12 weeks.
*What method used for propagation.*—Unrooted cuttings.
*Time to initiate roots.*—3 weeks.

Basal stems:
*Basal stem width dimensions.*—13 mm.
*Basal stem shape.*—Round.
*Basal stem surface.*—Slightly rough.
*Basal stem color.*—199B.

Branches:
*Branching habit.*—Lateral.
*Internode length.*—0.5 inches.
*Stem length dimensions.*—12 inches Stem shape: Round.
*Stem surface.*—Slightly rough.
*Stem color* (*new growth*).—152A.
*Stem color* (*mature growth*).—175A.
*Stem strength.*—Firm.

Leaves:
*Type.*—Deciduous.
*Leaf arrangement.*—Alternating.
*Quantity of leaves.*—2,640.
*Leaf division.*—Simple.
*Leaf aspect.*—Serrate.
*Leaf shape.*—Oblanceolate.
*Leaf base.*—Cuneate.
*Leaf apex.*—Acute.
*Leaf venation.*—Pinnately netted.
*Vein aspect* (*raised or depressed*).—Raised.
*Leaves* (*new growth*).—Leaf dimensions: 4 cm×1 cm. Leaf color (upper surface): 144A. Leaf color (lower surface): 143A. Vein color (upper surface): 145B. Vein color (lower surface): 145B. Leaf surface texture (upper): Smooth with slight resistance. Leaf surface texture (lower): Smooth with slight resistance. Petiole dimensions: 3 mm. Petiole shape: Circular. Petiole: Surface smooth. Petiole color: 145B.
*Leaves* (*mature growth*).—Leaf dimensions (mature growth): 8 cm×2 cm. Leaf color (upper surface): 137A. Leaf color (lower surface): 146B. Vein color (upper surface): 145B. Vein color (lower surface): 145B. Leaf surface texture (upper): Smooth with slight resistance. Leaf surface texture (lower): Smooth with slight resistance. Petiole width dimensions: 4 mm. Petiole shape: Circular. Petiole surface: Smooth. Petiole color: 146D. Leaf margin: Serrated. Teeth quantity and dimensions: 6 teeth, 1 cm long.

Flower description: Flower development has not been observed on plants of the new Wax Myrtle.

Disease and environmental resistance:
*Very heat and humidity tolerant.*
*No diseases observed to date.*

COMPARISON WITH KNOWN VARIETY

The closest variety of Wax Myrtle known to the inventors is the Wax Myrtle variety 'Don's Dwarf' (unpatented). In comparison with 'Don's Dwarf', the 'JBG 1000' branches a little more freely instead of having a perfectly mounded habit. The foliage of 'JBG 1000' is lighter green in color and is highly vigorous, and the mature size of 'JBG 1000' is significantly larger than the 'Don's Dwarf'.

I claim:

1. A new and distinct cultivar of Wax Myrtle Plant Named 'JBG 1000' as described and illustrated herein.

* * * * *